(12) United States Patent
Holenstein et al.

(10) Patent No.: US 8,470,267 B2
(45) Date of Patent: Jun. 25, 2013

(54) APPARATUS FOR SEPARATING MAGNETIC PARTICLES FROM LIQUIDS CONTAINING SAID PARTICLES, AND AN ARRAY OF VESSELS SUITABLE FOR USE WITH SUCH AN APPARATUS

(75) Inventors: Tobias Holenstein, Kuessnacht am Rigi (CH); Rolf Schneebeli, Mettmenstetten (CH); Renato Belz, Emmenbrucke (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 448 days.

(21) Appl. No.: 12/294,509

(22) PCT Filed: Mar. 21, 2007

(86) PCT No.: PCT/EP2007/002491
§ 371 (c)(1), (2), (4) Date: Jun. 28, 2010

(87) PCT Pub. No.: WO2007/112862
PCT Pub. Date: Oct. 11, 2007

(65) Prior Publication Data
US 2010/0284864 A1 Nov. 11, 2010

(30) Foreign Application Priority Data

Mar. 31, 2006 (EP) ..................................... 06075785

(51) Int. Cl.
*B03C 1/12* (2006.01)
(52) U.S. Cl.
USPC ........... 422/549; 422/551; 422/552; 422/562; 422/564; 422/929; 435/288.1; 435/304.1; 435/294.1; 436/810
(58) Field of Classification Search
USPC ................. 422/549, 551, 552, 562, 564, 929; 435/288.1, 304.1, 294.1; 436/810
See application file for complete search history.

(56) References Cited

U.S. PATENT DOCUMENTS

| 6,187,270 B1 | 2/2001 | Schmitt et al. |
| 6,579,453 B1 | 6/2003 | Bachler et al. |

(Continued)

FOREIGN PATENT DOCUMENTS

| EP | 0965385 B1 | 12/1999 |
| EP | 1449551 A1 | 5/2004 |

(Continued)

OTHER PUBLICATIONS

Translation for EP1449551.*

(Continued)

*Primary Examiner* — Brian R Gordon
*Assistant Examiner* — Shogo Sasaki
(74) *Attorney, Agent, or Firm* — M. Reza Savari

(57) ABSTRACT

An apparatus for separating magnetic particles from a liquid which contains said particles, said liquid being contained in an elongated vessel (11) having a length axis (12), said vessel being arranged in a vessel holder (13) with its length axis (12) in a substantially vertical position, said vessel (11) having a bottom and a tapered cross-section that diminishes towards the bottom of the vessel and a side wall (14) which has an outer surface which forms an angle with the length axis (12) of said vessel (11). This apparatus comprises a magnet (15) having a plane outer surface (16) and being adapted for being moved by transport means (17) along a motion path (25), said magnet (15) and said transport means (17) being so arranged with respect to said vessel (11) that over a portion of said motion path (25) said plane outer surface (16) of said magnet is in contact with a portion of said outer surface of said side wall (14) of said vessel (11), and transport means (17) for moving said magnet (15) between a first predetermined position and a second predetermined position along said motion path (25).

3 Claims, 9 Drawing Sheets

U.S. PATENT DOCUMENTS

2004/0195193 A1 10/2004 Jafari et al.
2005/0013741 A1 1/2005 a'Brassard

FOREIGN PATENT DOCUMENTS

| EP | 1441225 A1 | 7/2004 |
| EP | 1499551 B1 | 8/2006 |
| EP | 06075785 | 8/2006 |
| WO | 03095348 A1 | 11/2003 |
| WO | 03097240 A2 | 11/2003 |

OTHER PUBLICATIONS

1993, "Merriam-Webster's Collegiate Dictionary, Tenth Edition", Merriam-Webster, Incorporated, 281.

Gibson, Carol, Ed., 1990, "The Pan Dictionary of Mathematics", Pan Books Limited, 46-47.

* cited by examiner

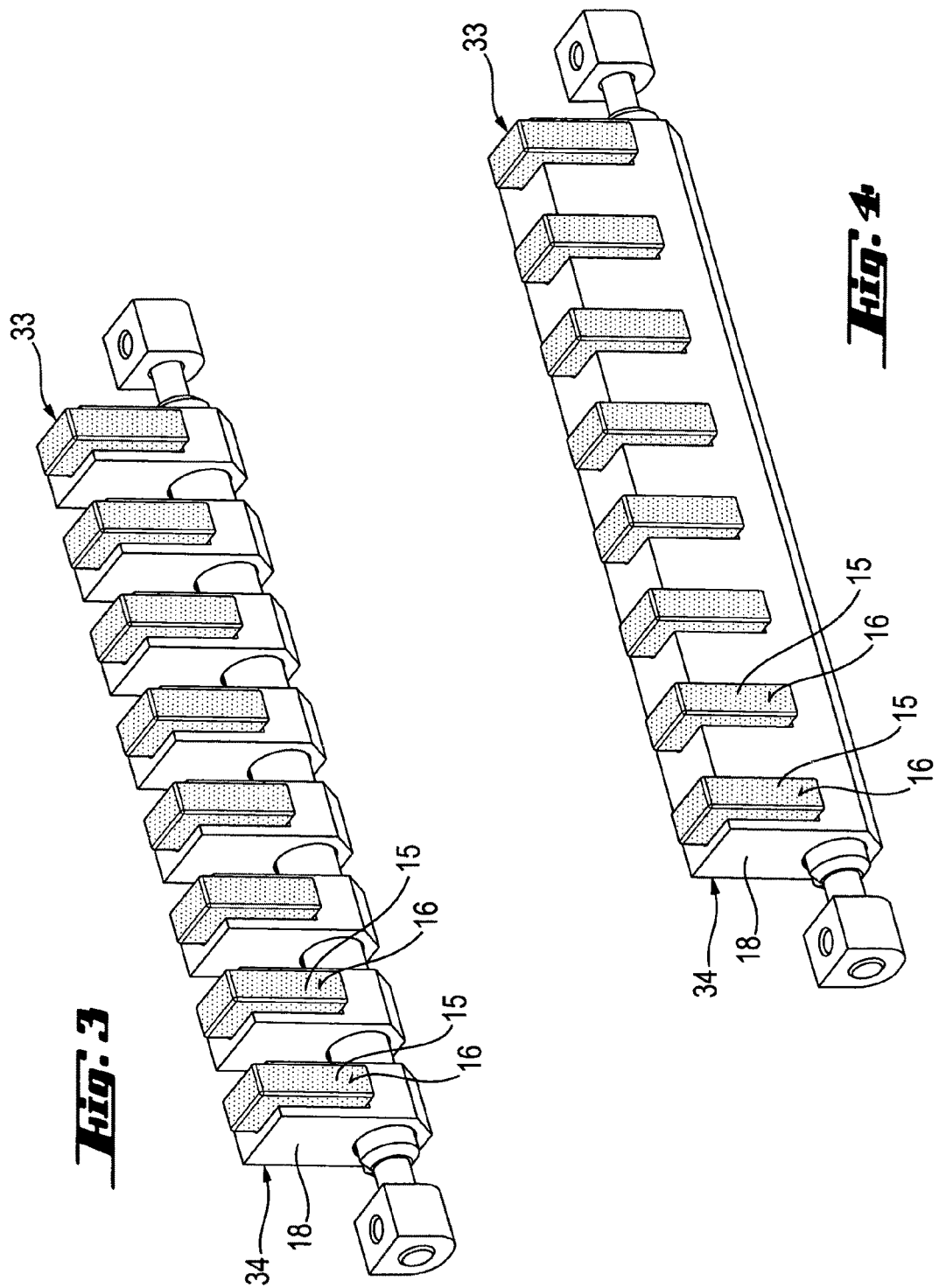

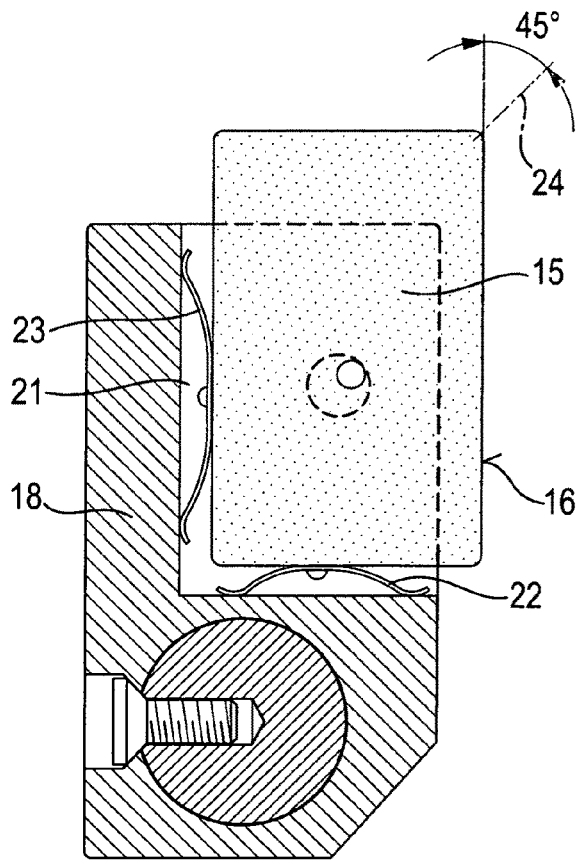
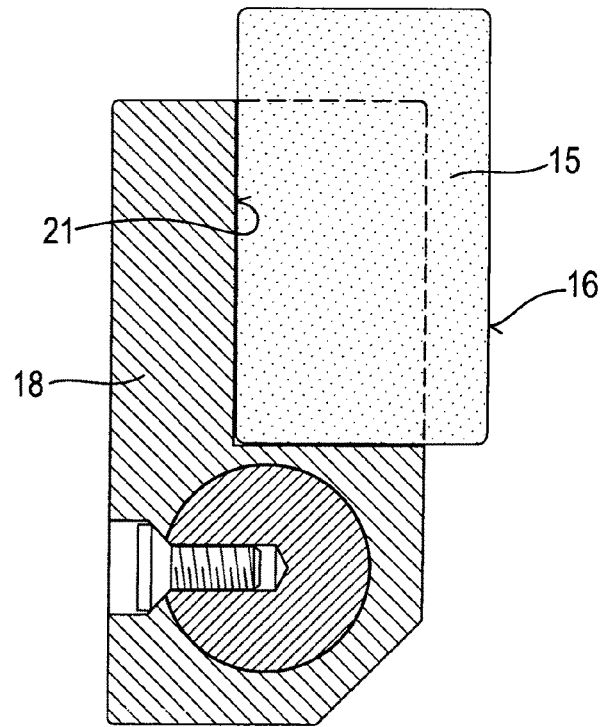

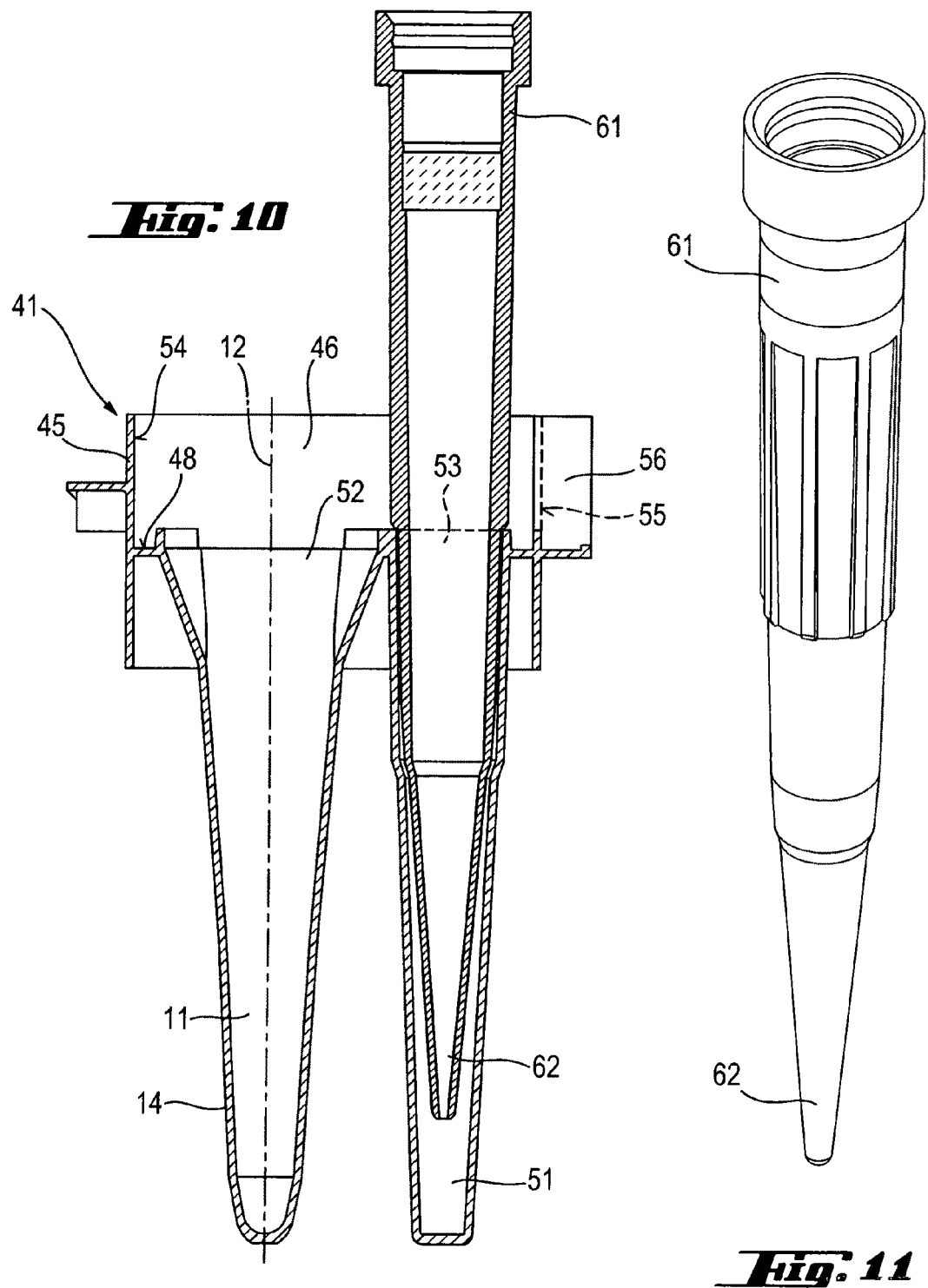

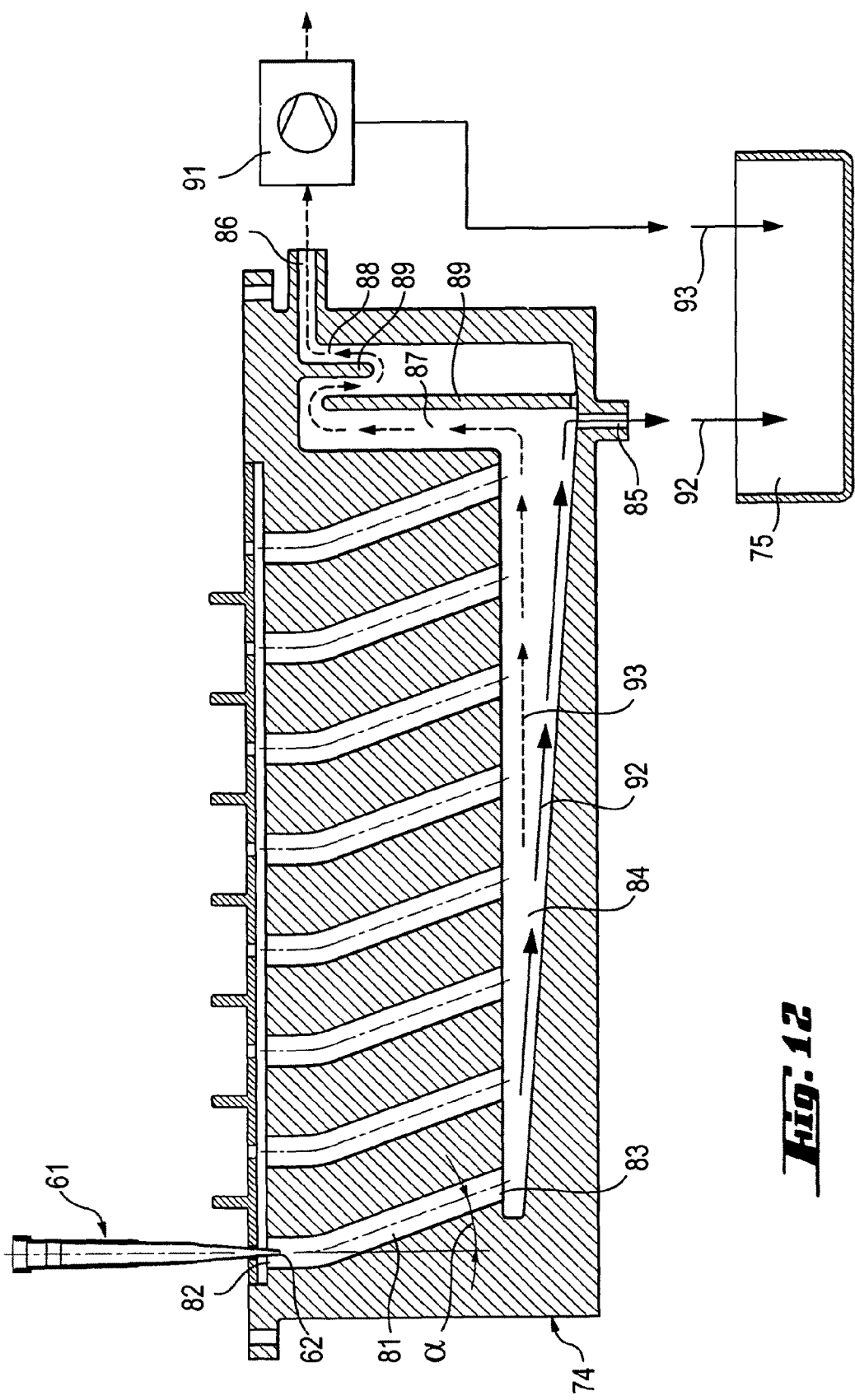

APPARATUS FOR SEPARATING MAGNETIC PARTICLES FROM LIQUIDS CONTAINING SAID PARTICLES, AND AN ARRAY OF VESSELS SUITABLE FOR USE WITH SUCH AN APPARATUS

CROSS-REFERENCES TO RELATED APPLICATIONS

The present application claims the benefit of EP Appl. No. 06075785.3 filed Mar. 31, 2006, the entire contents of which is hereby incorporated herein by reference in its entirety.

FIELD OF THE INVENTION

The present application relates to the field of devices for magnetic separation of an analyte from a liquid sample as used for example in immuno- or nucleic acid diagnostic assays.

BACKGROUND OF THE INVENTION

Magnetic particles are used as solid phase for performing some diagnostic assays, e.g. immunoassays. Such assays comprise magnetic particles in suspension in a reaction solution contained in a vessel. When the assay is conducted, it is at some steps necessary to separate the magnetic particles from the liquid contained in the vessel.

In a known apparatus this is done by attracting the magnetic particles to the walls of the vessel by means of a magnet positioned close to the outer side wall of the vessel and by extracting the liquid from the vessel by suitable means.

In an apparatus of this kind described in U.S. Pat. No. 6,187,270 a pipetting tip is used as a vessel and a magnet is located close to a wall of the pipetting tip in order to fix a cluster of magnetic particles at a given position on the inner surface of that wall of the pipetting tip. With the cluster of magnetic particles in that position washing water is drawn into the pipetting tip for performing a washing step. This water is ejected from the pipetting tip and another portion of fresh water is drawn in. After that the pipetting tip is slowly moved away from the magnet for moving the magnetic particles towards the tip of the pipetting tip.

According to U.S. Pat. No. 6,187,270 a stationary magnet is used and an apparatus for moving the pipetting tip with respect to the magnet is used for carrying out the above described motion of the pipetting tip. A disadvantage of the latter apparatus is that the magnetic force that acts on the magnetic particles rapidly diminishes as the pipetting tip is moved away from the magnet, and the desired transport of the magnetic particles to the tip of the pipetting tip is thus relatively slow.

Another disadvantage of an apparatus of the kind described in U.S. Pat. No. 6,187,270 is that when it is desired to process in parallel liquids contained in a plurality of vessels, a corresponding plurality of transport means for moving the vessels away from the magnets are required.

SUMMARY OF THE INVENTION

In a first aspect the invention relates to a method for separating magnetic particles from a liquid which contains said particles, said liquid being contained in an elongated vessel, said method comprising automatically moving a magnet along a motion path with respect to said elongated vessel, wherein the elongated vessel has a length axis and is arranged in a vessel holder with its length axis in a substantially vertical position, said vessel having a bottom and a lower portion which has a tapered cross-section that diminishes towards the bottom of the vessel and a side wall which has an outer surface which forms an angle with the length axis of said vessel, and wherein, the magnet has a plane outer surface in contact with a portion of the outer surface of the side wall of the lower portion of said vessel over a portion of said motion path, and wherein the magnet is moved downwards and towards the length axis of said vessel, when it is moved along said portion of said motion path.

In another aspect, the invention relates to an apparatus for separating magnetic particles from a liquid which contains said particles, said apparatus comprising an elongated vessel which contains said elongated vessel having a length axis and a bottom, said vessel being arranged in a vessel holder with its length axis in a substantially vertical position, said vessel having a lower portion which has a tapered cross-section that diminishes towards the bottom of the vessel and a side wall which has an outer surface which forms an angle with the length axis of said vessel, a magnet having a plane outer surface and being adapted for being moved by transport means along a motion path, said magnet and said transport means being so arranged with respect to said vessel that over a portion of said motion path said plane outer surface of said magnet is in contact with a portion of said outer surface of said side wall of said lower portion of said vessel, and transport means for moving said magnet between a first predetermined position and a second predetermined position along said motion path, said motion path being so arranged that said magnet is moved downwards and towards the length axis of said vessel when said magnet is moved from said first predetermined position to said second predetermined position along said motion path.

In a further aspect, the invention relates to an array of vessels suitable for containing liquid samples to be processed in an analyzer, said array comprising (a) an upper part having a substantially cuboid shape and comprising compartments each having a bottom wall that comprises a first opening and a second opening; (b) a first row of vessels for receiving said samples, wherein each of the first row of vessels integrally extend from the first opening of the bottom wall of each of the compartments; and (c) a second row of vessels each adapted for receiving a pipetting tip, wherein each of the second row of vessels integrally extend from the second opening of the bottom wall of each of the compartments; wherein, each of said compartments comprise a back side wall and a front side wall each rising from the bottom wall, the front side wall being located in face of the back side wall, said compartments being separated from each other by dividing side walls which extend between the back side wall and the front side wall of each compartment wherein the first and the second openings of the bottom wall are not separated from each other by a wall which extends across the dividing side walls, and each of said front side walls having a central opening for passage of a tip of the pipetting tip from a position within the array of vessels to a position outside the array of vessels.

In yet another aspect, the invention relates to an apparatus for separating magnetic particles from a plurality of liquids which contain said particles, each of said liquids being contained in a vessel which is part of an array of vessels, an array of vessels according to the invention and a connecting device for connecting said array of vessels to means for disposal of waste liquids contained in vessels of said array of vessels.

BRIEF DESCRIPTION OF THE FIGURES

FIG. 3 shows a perspective view of an array 34 of a first embodiment of magnet holders 18 each of which holds a magnet 15.

FIG. 4 shows a perspective view of a second embodiment of a magnet holder 18 for holding a plurality of magnets 15.

FIG. 5 shows a cross-sectional view of a first embodiment of a magnet holder 18 shown in FIG. 1 and of a magnet 15 inserted thereinto.

FIG. 6 shows a cross-sectional view of a second embodiment of a magnet holder 18 shown in FIG. 1 and of a magnet 15 inserted thereinto.

FIG. 10 shows a cross-sectional view of vessel array 41.

FIG. 11 shows a perspective view of a pipetting tip 61, as shown in FIGS. 1 and 2.

FIG. 12 shows a schematic cross-sectional view of a certain embodiment of the lower part 74 of waste connector 71.

DETAILED DESCRIPTION OF THE INVENTION

Figure 1:
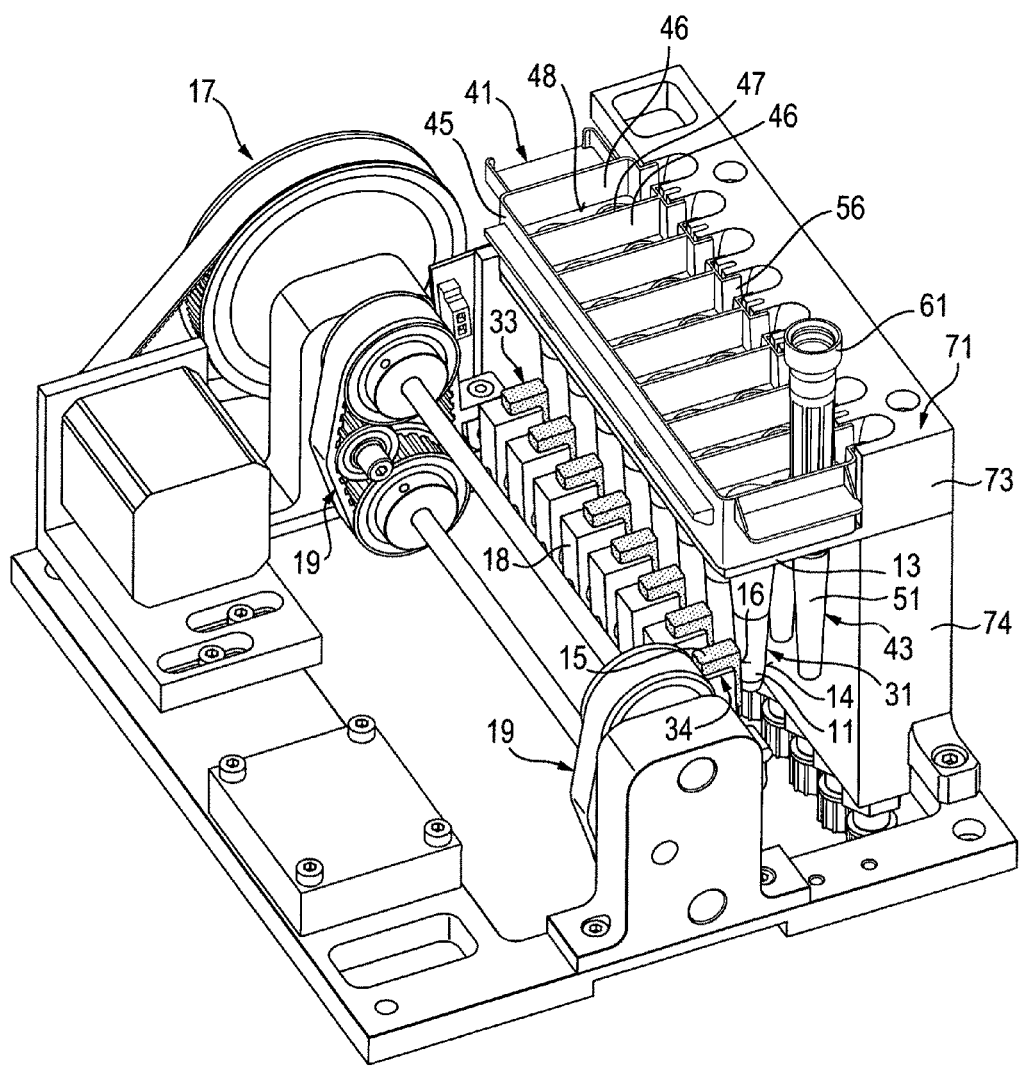
FIG. 1 shows a perspective view of an apparatus according to the invention.

A first aim of the invention is therefore to provide a method and an apparatus which makes possible to transport magnetic particles within a vessel more rapidly.

A second aim of the invention is to provide a method and an apparatus which makes it possible to achieve the above mentioned first aim simultaneously in a plurality of vessels.

A third aim of the invention is to provide an apparatus which in addition to achieving the above-mentioned second aim makes possible the removal of waste liquids contained in a plurality of vessels with more simple means than in prior art.

A fourth aim of the invention is to provide an array of vessels suitable for use with apparatus of the above-mentioned kind.

According to a first aspect of the invention the above-mentioned first aim is achieved with a method according to claim 1 and with an apparatus according to claim 4. Further embodiments of the latter method are defined by claims 2 and 3. Further embodiments of the apparatus according to claim 4 are defined by claims 5 to 9.

According to a third aspect of the invention the above-mentioned third aim is achieved with an apparatus according to claim 12.

According to a fourth aspect of the invention the above-mentioned fourth aim is achieved with a vessel array according to claim 10. A certain embodiment of this vessel array is defined by claim 11.

The apparatuses according to the invention offer the advantage of providing the possibility of carrying out washing steps of the above-described type more rapidly, more effectively and with more efficient means, in particular in the case of parallel processing of liquids which contain magnetic particles and which are contained in a plurality of vessels.

The vessel array according to the invention is particularly advantageous for use with an apparatus according to the second aspect of the invention.

The term "cuboid" means approximately cubical in shape, as defined in Merriam-Webster Collegiate Dictionary, Tenth Edition.

The invention concerns a method for separating magnetic particles from a liquid which contains said particles, said liquid being contained in an elongated vessel having a length axis, said vessel being arranged in a vessel holder with its length axis in a substantially vertical position, said vessel having a bottom and a lower portion which has a tapered cross-section that diminishes towards the bottom of the vessel and a side wall which has an outer surface which forms an angle with the length axis of said vessel.

The invention further concerns a method for separating magnetic particles from a plurality of liquids which contain said particles, each of said liquids being contained in an elongated vessel which has a length axis and which is part of an array of vessels, the vessels of said array of vessels being arranged in a vessel holder with their length axis in a substantially vertical position, each of said vessels having a bottom and a lower portion which has a tapered cross-section that diminishes towards the bottom of the vessel and a side wall which has an outer surface which forms an angle with the length axis of said vessel.

The invention also concerns an apparatus for separating magnetic particles from a liquid which contains said particles, said liquid being contained in an elongated vessel having a length axis, said vessel being arranged in a vessel holder with its length axis in a substantially vertical position, said vessel having a bottom and a lower portion which has a tapered cross-section that diminishes towards the bottom of the vessel and a side wall which has an outer surface which forms an angle with the length axis of said vessel.

The invention further concerns an apparatus for separating magnetic particles from a plurality of liquids which contain said particles, each of said liquids being contained in an elongated vessel which has a length axis and which is part of an array of vessels, the vessels of said array of vessels being arranged in a vessel holder with their length axis in a substantially vertical position, each of said vessels having a bottom and a lower portion which has a tapered cross-section that diminishes towards the bottom of the vessel and a side wall which has an outer surface which forms an angle with the length axis of said vessel The invention further concerns an array of vessels suitable for containing liquid samples to be processed in an apparatus of the above-described kind.

The subject invention will now be described in terms of its various embodiments with reference to the accompanying drawings. These embodiments are set forth to aid the understanding of the invention, but are not to be construed as limiting.

EXAMPLES

The following examples and figures are provided to aid the understanding of the present invention, the true scope of which is set forth in the appended claims. It is understood that modifications can be made in the procedures set forth without departing from the spirit of the invention.

Example 1

First Embodiment of an Apparatus According to the Invention

A first embodiment of an apparatus for separating magnetic particles from a liquid which contains such particles is described hereinafter with reference to FIGS. 1, 2, 5 and 6.

Figure 2:
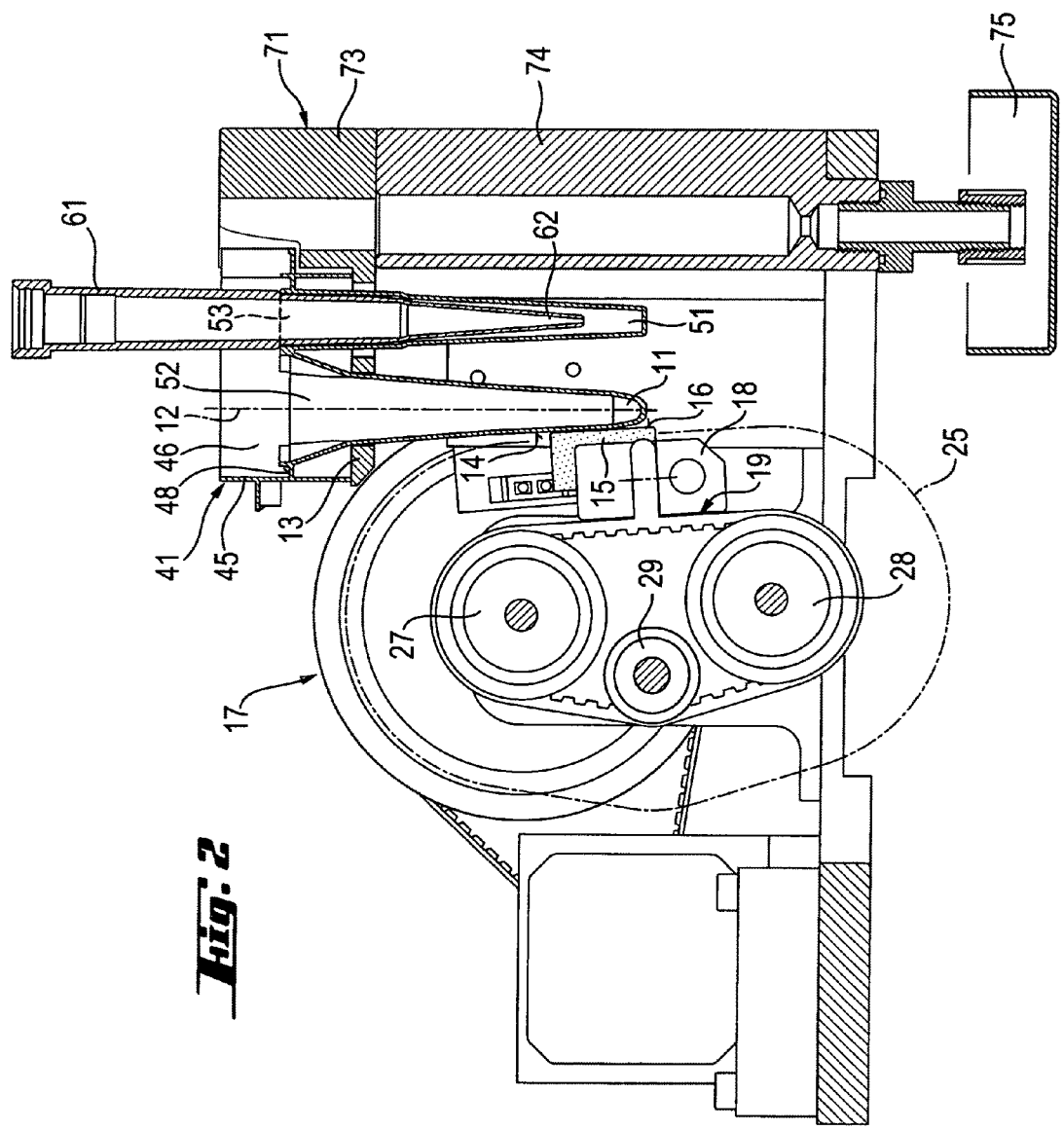
FIG. 2 shows a cross-sectional view of the apparatus shown in FIG. 1 in a plane passing through the length symmetry axis of vessel 11 in FIG. 1.

The apparatus shown in FIGS. 1 and 2 comprises a vessel holder 13. A liquid which contains magnetic particles is contained in an elongated vessel 11 shown in FIGS. 1 and 2.

Vessel 11 has a length symmetry axis 12 and has a lower portion which includes the bottom part of vessel 11. The lower portion of vessel 11 has a tapered cross-section that diminishes towards the bottom of the vessel. The lower portion of vessel 11 has a side wall 14. Side wall 14 has an outer surface which has a conical shape. Therefore, the intersection of the outer surface of side wall 14 with a plane that passes through the length axis 12 of vessel 11 forms a small angle with the length axis 12.

Vessel 11 is arranged in vessel holder 13 with the length axis 12 of vessel 11 in a substantially vertical position.

The apparatus shown in FIGS. 1 and 2 further comprises a magnet 15 which has a plane outer surface 16, and transport means 17 for moving magnet 15 along a motion path 25. As shown by FIG. 2, motion path 25 is for example a closed motion path.

Transport means 17 comprise a magnet holder 18 for receiving and holding a substantial portion of magnet 15 and a belt-drive 19 for moving magnet holder 18 and thereby magnet 15 along motion path 25. The structure of the belt drive includes tooth wheels 27 and 28 and a tension pulley 29 in the arrangement shown by FIG. 2. An initial tension of belt-drive 19 is achieved by adjustment of the position and radius of tension pulley 29.

Transport means 17 are adapted for moving magnet 15 between a first predetermined position and a second predetermined position along motion path 25. As shown by FIG. 2, the first predetermined position lies e.g. at about the same height as the central part of the lower portion of vessel 11, and the second predetermined position is e.g. close to the bottom of vessel 11.

Magnet 15 and transport means 17 are so arranged with respect to vessel 11 that while transport means 17 move magnet 15 along the portion of motion path 25 which extends from the first predetermined position to the second predetermined position, the plane outer surface 16 of magnet 15 is in contact with a portion of the outer surface of side wall 14 of the lower portion of vessel 11. Motion path 25 is so arranged that magnet 15 is moved downwards and towards the length axis 12 of vessel 11 when magnet 15 is moved from said first predetermined position to said second predetermined position along motion path 25.

As shown by FIGS. 5 and 6, magnet holder 18 has a cavity 21 for receiving a portion of magnet 15.

In a certain embodiment a portion of magnet 15 is arranged in and snuggly fits in a cavity 21 of magnet holder 18 as shown by FIG. 6. In this embodiment transport means 17 are so dimensioned that the initial tension of belt-drive 19 exerts on magnet 15 a force which presses it against side wall 14 and which is sufficient for ensuring contact of the plane outer surface 16 of magnet 15 and the outer surface of side wall 14 of the lower portion of vessel 11, when the magnet 15 is located between belt-drive and vessel 11 and moves along motion path 25.

In another embodiment of magnet holder 18 shown by FIG. 5, the structure of this holder includes leaf springs 22 and 23 arranged between magnet 15 and magnet holder 18. In this embodiment the force that presses magnet 15 against the outer surface of side wall 14 of the lower part of vessel 11 is the sum of the force resulting from the initial tension of belt drive 19 and the additional force exerted by leaf springs 22 and 23. The force resulting from this sum ensures a good contact of the plane outer surface 16 of magnet 15 and the outer surface of side wall 14 of the lower portion of vessel 11, when the latter is located between belt-drive and vessel 11 and moves along motion path 25.

As illustrated by FIG. 5, in a certain embodiment magnet 15 has a magnetic axis 24 that forms an angle of 45 degrees with plane outer surface 16 of the magnet 15.

Example 2

First Embodiment of a Method According to the Invention

A method for separating magnetic particles from a liquid which contains such particles can be carried out according to the invention with the apparatus embodiment of example 1 described above with reference to FIGS. 1, 2, 5 and 6. According to this method a magnet 15 having a plane outer surface 16 is moved automatically along a motion path 25 so that over a portion of motion path 25 which extends from the above-mentioned first predetermined position to the second predetermined position, the plane outer surface 16 of magnet 15 is in contact with a portion of the outer surface of side wall 14 of the lower portion of vessel 11, and magnet 15 is moved downwards and towards the length axis 12 of vessel 11, when it is moved along the above mentioned portion of motion path 25.

In a certain embodiment a force is exerted on magnet 15 in order to press the plane outer surface 16 of magnet 15 on the outer surface of the side wall 14 of the lower part of vessel 11 while magnet 15 is moved along the above-mentioned portion of motion path 25.

In a certain embodiment motion path 25 is a closed motion path.

Example 3

Second Embodiment of an Apparatus According to the Invention

A second embodiment of an apparatus for separating magnetic particles from a plurality of liquids which contain such particles is described hereinafter with reference to FIGS. 1 to 7.

The apparatus shown in FIGS. 1 and 2 comprises a vessel holder 13 adapted for receiving an array 31 of vessels 11. Each of the liquids which contain magnetic particles is contained in one of vessels 11.

Each vessel 11 has a length symmetry axis 12 and a lower portion which includes the bottom part of vessel 11. The lower portion of vessel 11 has a tapered cross-section that diminishes towards the bottom of the vessel. The lower portion of vessel 11 has a side wall 14. Side wall 14 has an outer surface which has a conical shape. The intersection of the outer surface of side wall 14 with a plane that passes through the length axis 12 of vessel 11 forms a small angle with the length axis 12.

The vessels 11 of array 31 are arranged in vessel holder 13 with their length axis in a substantially vertical position.

The apparatus shown in FIGS. 1 and 2 further comprises an array 33 of magnets 15 each of which has a plane outer surface 16, and transport means 17 for moving each magnet of array 33 of magnets along a motion path 25. As shown by FIG. 2, motion path 25 is for example a closed motion path.

Transport means 17 comprise an array 34 of magnet holders 18, each of which is adapted for receiving and holding a substantial portion of a magnet 15, and a belt-drive 19 for moving the array 33 of magnet holders 18 and thereby magnets 15 of array 33 of magnets 15 along motion path 25.

FIG. 3 shows a first embodiment of an array 34 of magnet holders which comprises individual magnet holders 18 which are rigidly connected with each other and each of which holds a magnet 15.

FIG. 4 shows a second embodiment of an array 34 of magnet holders which comprises a single body which has a plurality of cavities each of which is adapted for holding a magnet 15.

Transport means 17 are adapted for moving each magnet 15 between a first predetermined position and a second predetermined position along motion path 25. As shown by FIG. 2, the first predetermined position lies e.g. at about the same height as the central part of the lower portion of a corresponding vessel 11, and the second predetermined position is e.g. close to the bottom of that vessel 11.

The array 33 of magnets 15 and transport means 17 are so arranged with respect to the array 31 of vessels 11 that while transport means 17 move each of magnets 15 along the portion of motion path 25 which extends from the first predetermined position to the second predetermined position, the plane outer surface 16 of magnet 15 is in contact with a portion of the outer surface of side wall 14 of the lower portion of a corresponding vessel 11. Motion path 25 is so arranged that each magnet 15 is moved downwards and towards the length axis 12 of a corresponding vessel 11 when magnet 15 is moved from said first predetermined position to said second predetermined position along motion path 25.

As shown by FIGS. 5 and 6, each magnet holder 18 has a cavity 21 for receiving a portion of a magnet 15.

In a certain embodiment a portion of magnet 15 is arranged in and snuggly fits in a cavity 21 of magnet holder 18 as shown by FIG. 6. In this embodiment transport means 17 are so dimensioned that the initial tension of belt-drive 19 exerts on magnet 15 a force which presses it against side wall 14 and which is sufficient for ensuring contact of the plane outer surface 16 of magnet 15 and the outer surface of side wall 14 of the lower portion of vessel 11, when the magnet 15 is located between belt-drive and vessel 11 and moves along motion path 25.

In another certain embodiment of magnet holder 18 shown by FIG. 5, the structure of this holder includes leaf springs 22 and 23 arranged between magnet 15 and magnet holder 18. In this embodiment the force that presses magnet 15 against the outer surface of side wall 14 of the lower part of vessel 11 is the sum of the force resulting from the initial tension of belt drive 19 and the additional force exerted by leaf springs 22 and 23. The force resulting from this sum ensures a good contact of the plane outer surface 16 of magnet 15 and the outer surface of side wall 14 of the lower portion of vessel 11, when the latter is located between belt-drive and vessel 11 and moves along motion path 25.

As illustrated by FIG. 5, in a certain embodiment magnet 15 has a magnetic axis 24 that forms an angle of 45 degrees with plane outer surface 16 of the magnet 15.

Figure 7:
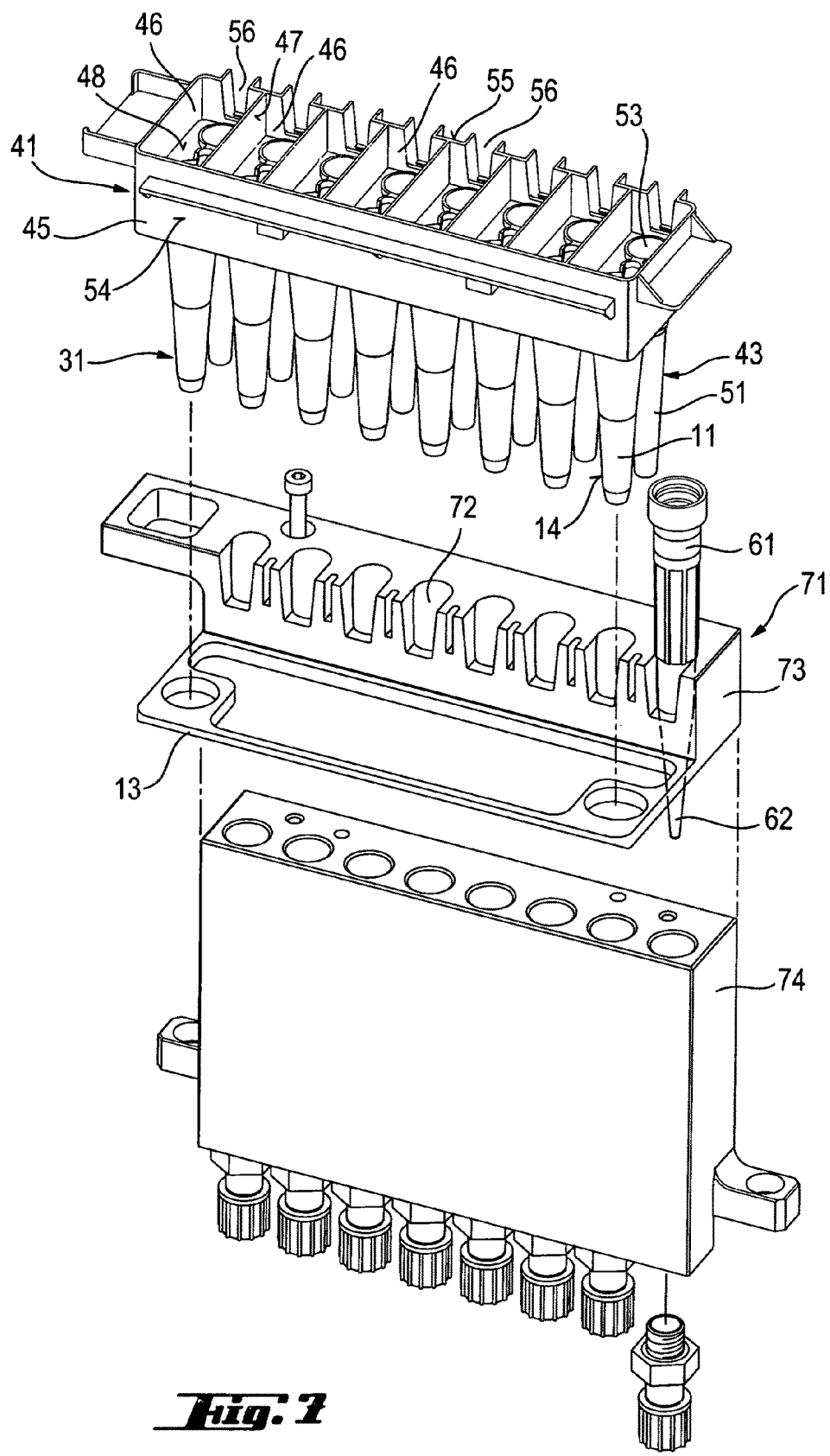
FIG. 7 shows a first, exploded perspective view of a vessel array 41 according to the invention, waste connector 71 and pipetting tip 61.

A certain embodiment of the apparatus described above with reference to FIGS. 1-6 further includes a waste connector or waste connecting device 71 shown in FIGS. 1, 2 and 7 for connecting array 31 of vessels 11 to a waste container 75 which serves for disposing of waste liquids contained in vessels 11 of array 31 of vessels. Waste connector 71 comprises an upper part 73 and a lower part 74. Upper part 73 of waste connector 71 includes the above-mentioned vessel holder 13 and cavities 72 each of which is adapted for receiving a pipetting tip 61 during delivery of waste liquid from tip 61 to a waste chamber 75 fluidically connected to the lower part 74 of waste connector 71. Waste connector 71 makes it possible to deliver waste liquids which arise in various vessels 11 to a waste container 75. The transfer of a waste liquid arising in a given vessel 11 to waste connector 71 and thereby to waste container 75 is carried out with a pipetting tip 61 which is operatively associated with that vessel.

FIG. 12 shows a certain embodiment of the lower part 74 of waste connector 71.

Lower part 74 of waste connector 71 has a plurality of bores 81, which have each an upper opening 82 adapted for receiving the tip 62 of a pipetting tip 61 and lower opening 83 which fluidically connects the bore 81 with a channel 84. Each of bores 81 has a short vertical portion which extends downwards from the upper opening of the bore along a vertical axis and a portion which extends along an axis which forms an angle α of about 20 degrees with the vertical axis. This structure offers the advantage that a liquid jet delivered by a pipetting tip 61 impacts on a surface which forms a slight angle with the axis of the jet. This prevents that waste liquid can splash outside of the bore during delivery of waste liquid from the pipetting tip to the waste connector.

The above described structure of waste connector 71 shown by FIG. 12 offers the following advantages:
  splash of waste liquid is prevented during delivery of waste liquid from the pipetting tip to the waste connector,
  contamination between pipetting tips is prevented, and
  contamination between pipetting tips and the waste connector is prevented.

Lower part 74 of waste connector 71 has an outlet 85 located at the lowest point of channel 84. Liquid collected in channel 84 can thus leave waste connector 71 through outlet 85 and drop into a waste container 75 following a path indicated by arrow 92.

In a certain embodiment of lower part 74 of waste connector 71 outlet 85 is closed by a suitable closure (not shown) and lower part 74 has an outlet 86 located close to the top portion of lower part 74 and a channel formed by channel portions 87 and 88 which are separated from each other by walls 89. In this embodiment, outlet 86 is fluidically connected to an aspiration pump 91 which delivers liquid aspirated from channel 84 through channels 87, 88 and outlet 86 to waste container 75. Arrows 93 show the path followed by liquid aspirated from channel 84 and delivered to waste container 75 as just described. This embodiment advantageously removes aerosols that may arise in the interior of waste container 71.

Example 4

Embodiment of an Array of Vessels Suitable for Use in an Apparatus According to the Invention An embodiment of array 41 of vessels suitable for use in an apparatus of the kind described above with reference to FIGS. 1-7 is described hereinafter with reference to FIGS. 8 to 11.

Figure 8:
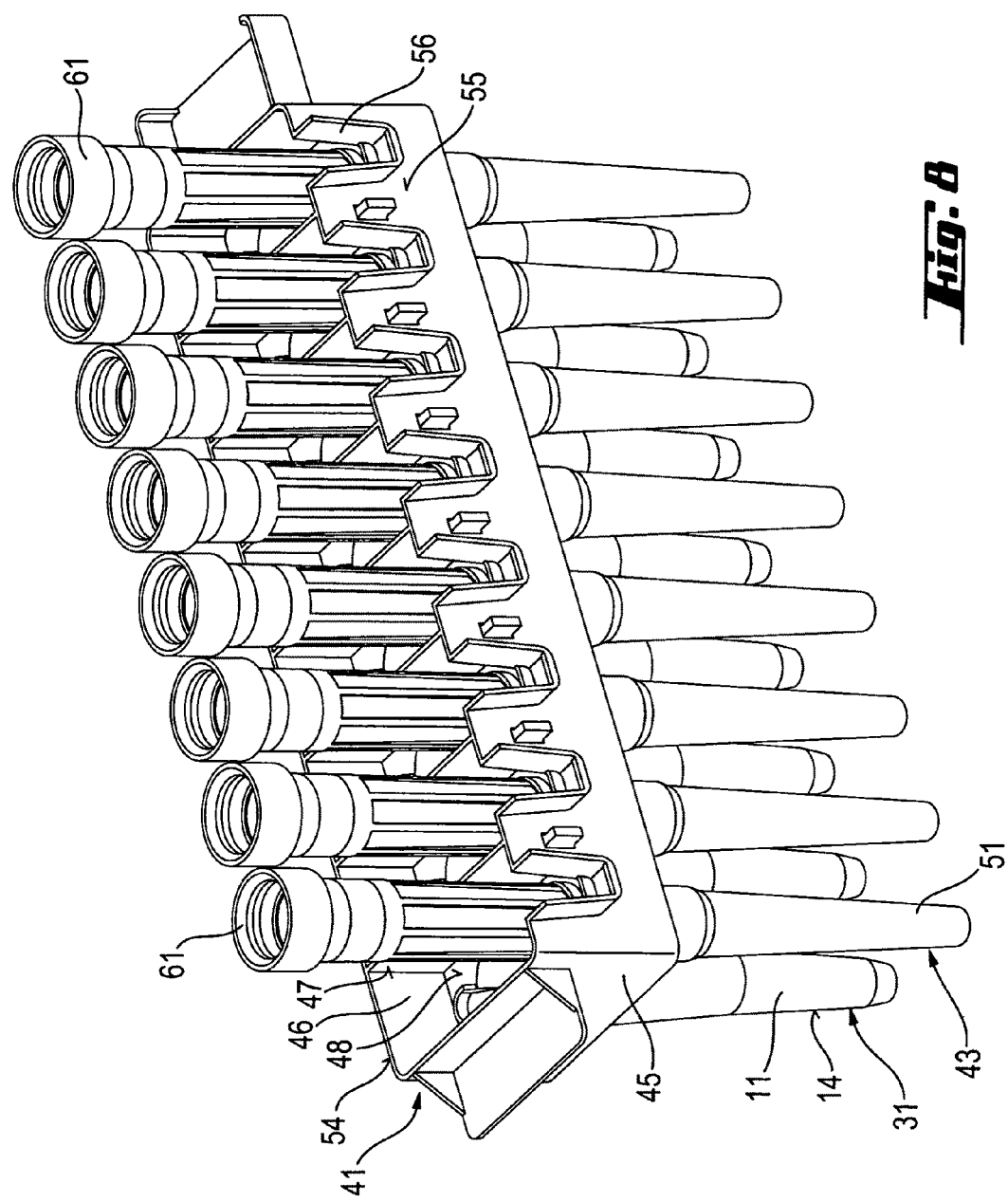
FIG. 8 shows a perspective view of a vessel array 41 according to the invention with pipetting tips 61 inserted in respective vessels 51 each of which is adapted for receiving a pipetting tip.

FIG. 8 shows a perspective view of a vessel array 41 according to the invention with pipetting tips 61 inserted in respective vessels 51 each of which is adapted for receiving a pipetting tip.

Figure 9:
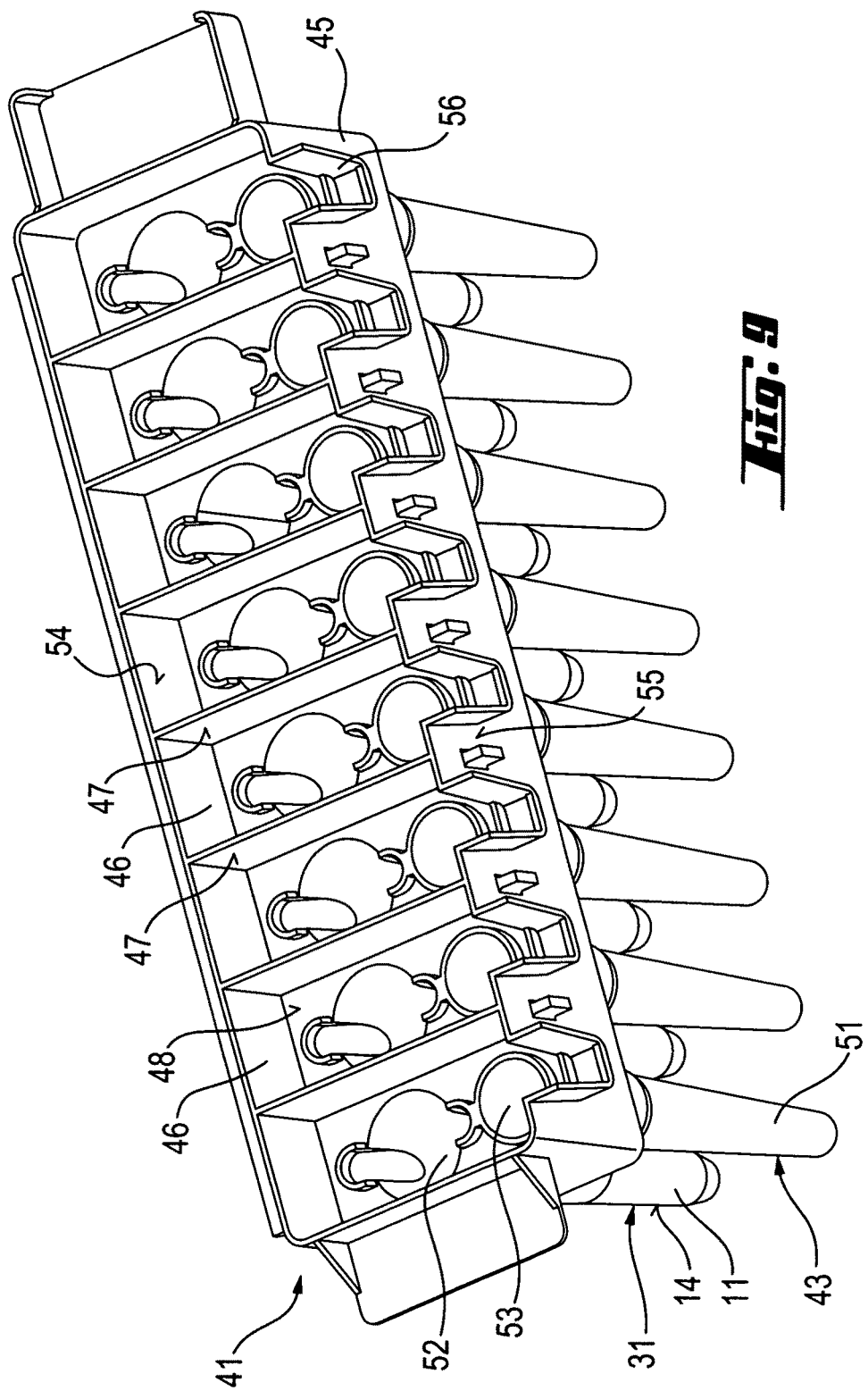
FIG. 9 shows a second perspective view of a vessel array 41 according to the invention.

FIG. 9 shows a second perspective view of a vessel array 41 according to the invention.

FIG. 10 shows a cross-sectional view of vessel array 41.

FIG. 11 shows perspective view of a pipetting tip 61 shown in FIGS. 1 and 2.

Vessel array 41 comprises a first row 31 of vessels 11 for receiving samples and a second row 43 of vessels 51 each of which is adapted for receiving a pipetting tip 61.

Vessel array 41 further comprises an upper part 45 which has approximately a cuboid shape and is divided in compartments 46. Each compartment 46 has a substantially cuboid shape and being divided in compartments 46 bottom wall 48 and side walls 47. A vessel 11 for receiving a sample extends downwards from an opening 52 in the bottom of wall 48 of each compartment 46. A vessel 51 for receiving the lower part of a pipetting tip 61 extends downwards from an opening 53 in the bottom of wall 48 of each compartment 46.

Each compartment 46 has a back side wall 55 and a front side wall 54 located in face of the back side wall. Neighboring compartments 46 are separated from each other by side walls 47 which extend each between a back side wall and a front side wall of a compartment.

Front side wall 54 of each compartment 46 has a central opening 56 which allows the passage of the tip 62 of a pipetting tip 61 when the latter is moved from a position within the array of vessels 41 to a position outside the array of vessels 41, e.g. when after aspiration of waste liquid from a vessel 11, pipetting tip 61 is moved away from vessel 11 and towards a position located in waste connector 71, e.g. the position of pipetting tip 61 shown in FIG. 7.

In a certain embodiment of vessel array 41, the upper part 45 thereof is made by injection molding of a first plastic material, e.g. of polystyrene, and the first and second rows 31, 43 of vessels are made by injection molding of a second plastic material, of polypropylene, and the material of the upper part 45, e.g. polystyrene, is more rigid than the material of the first and second rows 31, 43 of vessels, e.g. polystyrene. The advantage of this selection of materials is that the resulting structure of vessel array is less prone to getting deformed due to the operation conditions, and due e.g. to changes of temperature of the environment.

Example 5

Second Embodiment of a Method According to the Invention

A method for separating magnetic particles from a liquid which contains such particles can be carried out according to the invention with the apparatus embodiment of example 3 described above with reference to FIGS. 1 to 7 and with the array of vessels of example 4 described above with reference to FIGS. 8 to 11.

According to this method an array 33 of magnets 15 each of which has a plane outer surface 16 is moved automatically so that each of magnets 15 is thereby moved along a motion path 25 so that over a portion of motion path 25 which extends from the above-mentioned first predetermined position to the second predetermined position, the plane outer surface 16 of each magnet 15 is in contact with a portion of the outer surface of side wall 14 of the lower portion of vessel 11, and each magnet 15 is moved downwards and towards the length axis 12 of a vessel 11, when it is moved along the above mentioned portion of motion path 25.

In a certain embodiment a force is exerted on each magnet 15 of the array 33 of magnets in order to press the plane surface 16 of each magnet on the outer surface of the side wall 14 of the lower part of a corresponding vessel 11 while magnet 15 is moved along the above-mentioned portion of motion path 25.

In a certain embodiment motion path 25 is a closed motion path.

Example 6

Embodiment of a System in which the Above Mentioned Apparatuses and Methods are Used A system of this kind comprises a conveyor (not shown in the attached drawings), e.g. a conveyor adapted for moving vessel array in three directions X-, Y, Z which are orthogonal to each other. The latter conveyor serves for automatically transporting an array of vessels 41 according to Example 4 and positioning that array in vessel holder 13 in the position shown in FIGS. 1 and 2. With array 41 of vessels in that position pipetting operations are carried out in each of vessels 11 with a corresponding pipetting tip 61 which when not in use rests inserted in a vessel 51 adjacent to vessel 11.

When waste liquid in a vessel 11 has to removed, pipetting tip 61 is automatically transported into vessel 11 for that purpose, the waste liquid is aspired into pipetting tip 61, this tip is then automatically transported towards waste connector 71 and placed there in the position shown in FIG. 7. With pipetting tip 61 in that position the waste liquid is ejected from the tip and into a collecting chamber inside waste connector 71. During transport of pipetting tip 61 from vessel 11 to waste connector 71 the lower part of tip 61 passes through one of the openings 56 in the back side wall 55 of vessel array 41.

Although certain embodiments of the invention have been described using specific terms, such description is for illustrative purposes only, and it is to be understood that changes and variations may be made without departing from the spirit or scope of the following claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. An array of vessels suitable for containing liquid samples to be processed in an analyzer, said array comprising:
   (a) an upper part having a substantially cuboid shape and comprising compartments each having a bottom wall that comprises a first opening and a second opening;
   (b) a first row of vessels for receiving said samples, wherein each of the first row of vessels integrally extend from the first opening of the bottom wall of each of the compartments; and
   (c) a second row of vessels each adapted for receiving a pipetting tip, wherein each of the second row of vessels integrally extend from the second opening of the bottom wall of each of the compartments;
   wherein, each of said compartments comprise a back side wall and a front side wall each rising from the bottom wall, the front side wall being located in face of the back side wall, said compartments being separated from each other by dividing side walls which extend between the back side wall and the front side wall of each compartment wherein the first and the second openings of the bottom wall are not separated from each other by a wall which extends across the dividing side walls, and each of said front side walls having a central opening for passage of a tip of the pipetting tip from a position within the array of vessels to a position outside the array of vessels.

2. The array of vessels according to claim 1, wherein the upper part is comprised of a first plastic material and the first row of vessels and the second row of vessels are comprised of a second plastic material, the material of said upper part being more rigid that the material of said first and second rows of vessels.

3. An apparatus for separating magnetic particles from a plurality of liquid samples which contain said particles, the apparatus comprising:
   (a) an array of vessels according to claim 1, and
   (b) a waste connecting device operatively connecting said array of vessels to a waste container for disposal of waste liquids contained in the first row of vessels for receiving said samples.

* * * * *

UNITED STATES PATENT AND TRADEMARK OFFICE
CERTIFICATE OF CORRECTION

PATENT NO.        : 8,470,267 B2
APPLICATION NO. : 12/294509
DATED             : June 25, 2013
INVENTOR(S)       : Holenstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1180 days.

Signed and Sealed this

Eighth Day of September, 2015

Michelle K. Lee
*Director of the United States Patent and Trademark Office*